US 6,681,762 B1

(12) United States Patent
Scheuch et al.

(10) Patent No.: US 6,681,762 B1
(45) Date of Patent: Jan. 27, 2004

(54) METHOD AND AN APPARATUS FOR PROVIDING A CONSTANT MEDICINE DOSE FOR AN INHALIC APPLICATION AT LOW INHALIC FLOW

(75) Inventors: Gerhard Scheuch, Gemünden (DE); Knut Sommerer, München (DE); Bernhard Müllinger, Huldessen (DE); Friedel Haas, Gauting (DE); Sascha Roeder, Ingolstadt (DE)

(73) Assignee: GSF-Forschungszentrum fur Umwelt und Gesundheit GmbH (DE)

( * ) Notice: Subject to any disclaimer, the term of this patent is extended or adjusted under 35 U.S.C. 154(b) by 0 days.

(21) Appl. No.: 09/527,096

(22) Filed: Mar. 16, 2000

(30) Foreign Application Priority Data

Mar. 19, 1999 (DE) .......................................... 199 12 461

(51) Int. Cl.[7] ............................................. A61M 11/00
(52) U.S. Cl. ............................ 128/200.14; 128/203.12; 128/203.24; 128/205.24; 137/455; 251/205; 251/118
(58) Field of Search ..................... 128/200.14, 200.24, 128/203.12, 203.11, 203.24, 204.18, 205.14, 205.24; 137/455, 505, 505.14; 251/12, 14, 43–46, 118, 121, 205, 335.1–335.3, 349

(56) References Cited

U.S. PATENT DOCUMENTS

| 3,966,440 A | * | 6/1976 | Roberts ................. 128/202.22 |
| 4,284,505 A | | 8/1981 | Pope, Jr. et al. |
| 4,350,477 A | | 9/1982 | Mazal |
| 4,573,640 A | | 3/1986 | Mehoudar |
| 4,754,751 A | * | 7/1988 | Mausteller et al. .... 128/201.25 |
| 4,756,508 A | | 7/1988 | Giachino et al. |
| 4,917,081 A | * | 4/1990 | Bartos ................... 128/205.12 |
| 5,858,569 A | | 1/1999 | Meacher et al. |

FOREIGN PATENT DOCUMENTS

| DE | 80 01 273 | 5/1980 |
| DE | 44 11 093 A1 | 10/1995 |
| DE | 195 04 750 A | 8/1996 |
| DE | 197 34 022 A1 | 2/1999 |
| EP | 0 341 573 A | 11/1989 |
| GB | 2 218 352 | 11/1989 |
| WO | 84/01293 A | 4/1984 |

OTHER PUBLICATIONS

European Search Report for EP/00105664, Jun. 23, 2000.
German Search Report for 199 12 461.2, Feb. 25, 2000.

* cited by examiner

Primary Examiner—Glenn K. Dawson
(74) Attorney, Agent, or Firm—Myers Bigel Sibley and Sajovec

(57) ABSTRACT

A device for flow rate limitation at low differential pressures, particularly for limiting the volumetric inhalation flow during inhalation of therapeutic aerosols, consists of a housing 11 including an aspiration orifice 14, an inhalation orifice 15 and a flow passage 23 disposed therebetween. The flow passage has a flat elongate cross-section with flexible large-area walls 18, 20 having a cross-sectional area adapted to be reduced, as a function of the differential pressure prevailing between the inhalation orifice and the aspiration orifice, as well as of the flexibility of the material of the walls, to a size appropriate for a predetermined volumetric maximum inhalation flow.

25 Claims, 5 Drawing Sheets

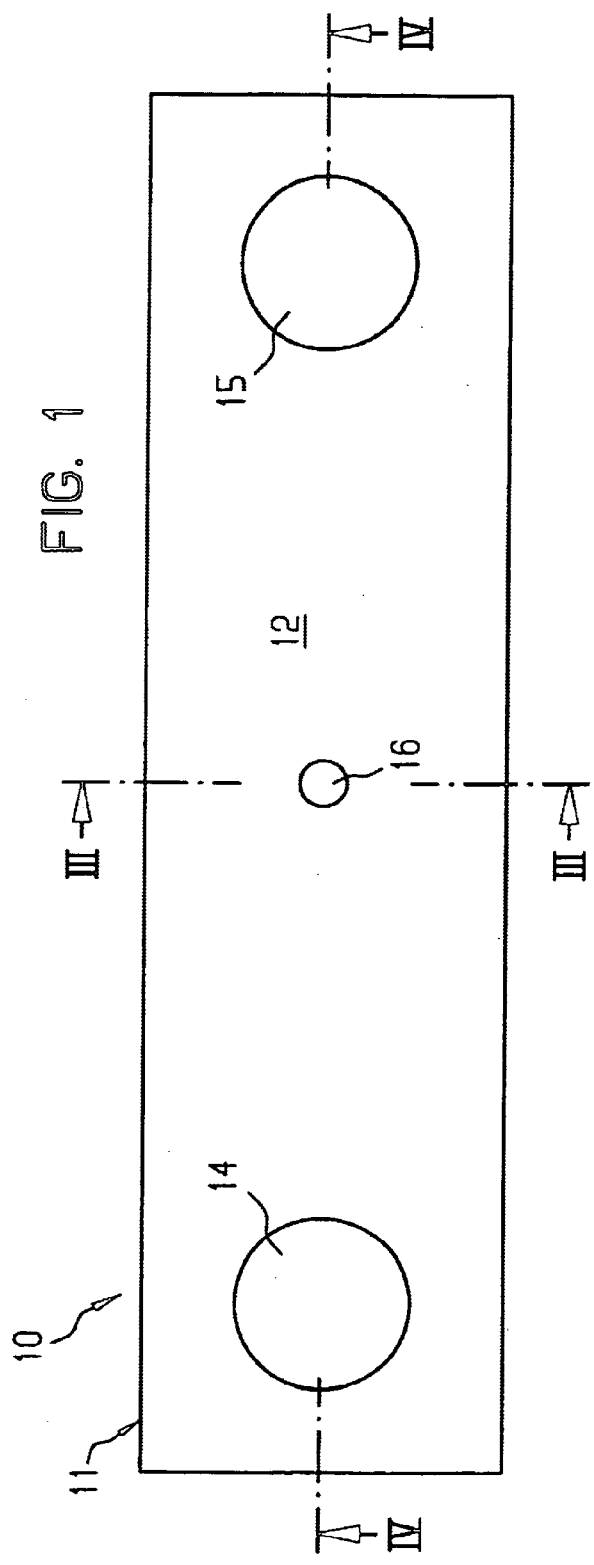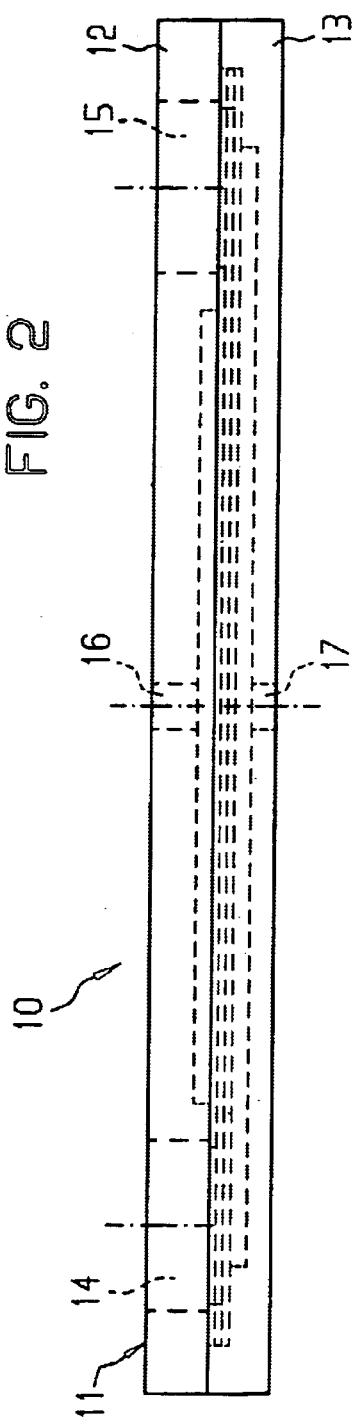

METHOD AND AN APPARATUS FOR PROVIDING A CONSTANT MEDICINE DOSE FOR AN INHALIC APPLICATION AT LOW INHALIC FLOW

RELATED APPLICATION

This application relates to German patent application no. 199 12 461.2 filed Mar. 19, 1999, the disclosure of which is incorporated herein by reference in its entirety.

FIELD OF THE INVENTION

The present invention relates to a device for flow rate limitation at low differential pressures, particularly for limiting the volumetric inhalation flow during inhalation of therapeutic aerosols.

BACKGROUND OF THE INVENTION

In the field of aerosol therapy it is important for the envisaged administration of the medicament that firstly a defined volumetric inhalation flow will not be exceeded and secondly that a pressure drop will occur at volumetric flows below the maximum volumetric flow, which is as low as possible. The flow rate limiting devices so far know fail to satisfy these conditions because in the majority of cases they operate only at pressures by far higher than 100 millibar above atmospheric pressure.

The present invention is intended to make a novel device available which is suitable for achieving a volumetric flow limitation as envisaged for the intended purpose during the inhalation of therapeutic aerosols.

SUMMARY OF THE INVENTION

This problem is solved In accordance with the present invention by the features defined in Patent claim 1. Preferred features which constitute expedient improvements of the invention may be taken from the dependent Claims.

Based on the inventive concept it is now possible in an expedient manner to make a device available for limiting the inhaled volume during the inhalation of therapeutic aerosols, wherein an automatic mechanical volumetric flow control commences at pressures as low as 5 millibar. On account of the selection of the flexibility or elasticity, respectively of the material for the wall sections of the flow passage, which bend inwards for narrowing the cross-section of the passage as a function of the subatmospheric pressure prevailing in the flow passage, it is now expediently possible at an extraordinarily low engineering expenditure to achieve an adaptation to various volumetric maximum flow rates. When moreover the material used for the production of the device consists of a biologically tolerable synthetic material, particularly when the flow passage is made of silicone, an excellent suitability for the clinical application is achieved.

In correspondence with a preferred embodiment the flow passage is configured to have a flat elongate cross-section which is formed to have opposing large-area walls. This configuration enhances the inward bending of the walls for a reduction of the cross-section of the passage.

In correspondence with a preferred further embodiment of the invention the opposing walls are open on their outside, at least in the central area between the aspiration and inhalation orifices, to the environment, with each wall having preferably one chamber section on its outside, which is open via a bore to the environment, at least in the central area between the aspiration and inhalation orifices. With these structural provisions the required pressure equalization is expediently ensured when the walls are contracted.

Moreover structurally simple provisions are made for a stratified structure of the flow passage, which comprises preferably a closed wall, a frame-shaped partition of the same size, and a wall of equal size with an aspiration and inhalation orifice, with the opposite walls being fastened on the sides of their edges in the housing.

Any flexible and biologically tolerable material is suitable for configuring the flow passage, which material is flexible and can also be returned into its original shape after bending. It is preferred that at least the large-area passage walls, preferably also the partition, consist of silicone mats whilst the housing is made of a preferably biologically tolerable synthetic material.

In correspondence with a special embodiment of the invention the material layers of the flow passage are fastened for exchange between two housing sections. With such a structure it is possible in a simple manner to use one device for different flow rate limiting parameters with a correspondingly associated flow passage. Each of the large-area passage walls has preferably the same thickness.

According to an alternative further embodiment of the invention expedient provisions are made for an integral structure of the flow passage, preferably in the form of a silicone element, instead of a stratified structure.

In correspondence with another embodiment of the invention provisions are made for a flow rate limitation independent of the environmental pressure, wherein each wall comprises on its outside a chamber section with a bore at least in the central area between the aspiration and inhalation orifices, which bores communicate with the aspiration orifice through a passage or a hose, respectively. With these provisions the differential pressure between the aspiration and inhalation orifices is measured, which is decisive for control, and flow rate limitation could also be operated in a closed system.

According to a further embodiment of the invention the flow passage may have an annular cross-section, instead of a flat elongate cross-section, with the flow passage being preferably symmetrically disposed in a cylindrical housing at a spacing from the inside cylinder wall, between radial disks. These retainer disks are preferably provided with aspiration and inhalation orifices having the shape of ring segments, with the retainer disk with the aspiration orifices having pressure equalizing bores for the cylindrical inside area and the annular zone surrounding the flow passage. This annular flow passage, too, is preferably formed of silicone.

In accordance with another alternative embodiment of the invention provisions are made for the formation of the flow region between a central inhalation orifice and aspiration orifices radially surrounding them which region presents star-shaped or radial webs extending from a common bottom surface to the flexible wall and forming flow passages which can be restricted. With these provisions the device can be designed with an extraordinarily compact structure, is easy to manufacture and to replace.

The webs forming flow passages may have different lengths so that in the region of the longer webs a wider flow passage will be formed which then splits into several flow passages at intermediately arranged shorter webs. The cross-section of the webs may be constant in a radial direction. The webs are expediently flaring outwardly over their width, with one aspiration orifice being preferably provided between two adjacent webs.

In an advantageous disposable embodiment, which is suitable for mass production, the device can be expediently realized with a disk-shaped basic body wherein the webs are integrally formed between flat recesses and inhalation orifices are formed on the edge side in the recesses, as well as with a thin flexible mat with a central aspiration orifice, which rests on the webs and is fastened in the edge region of the basic body. The mat may be adhesively fastened or welded, respectively, or clamped by means of an annular assembly element in the edge region of the basic body.

The thin flexible mat consists preferably of silicone, silicone rubber, Viton, latex, natural rubber or any other elastomer.

BRIEF DESCRIPTION OF THE DRAWINGS

Embodiments of the invention will now be described in more details in the following in a schematic form with reference to the attached drawing wherein:

FIG. 1 is a plan view of a device for limiting the volumetric inhalation flow rate during the inhalation of therapeutic aerosols;

FIG. 2 is a side view of the device illustrated in FIG. 1;

DESCRIPTION OF THE PREFERRED EMBODIMENTS

Figure 3:
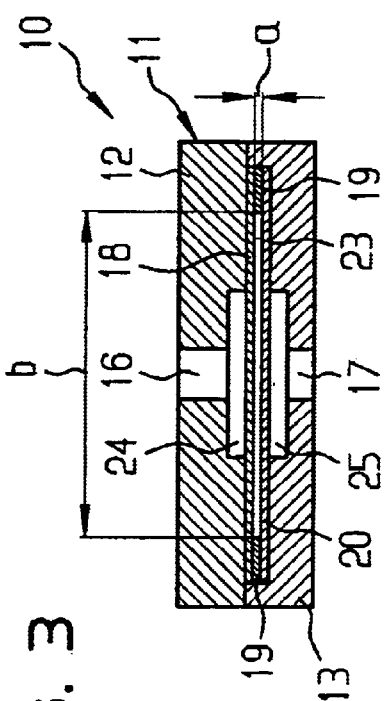
FIG. 3 shows a section taken along the line III—III in FIG. 1.

FIG. 1 shows one embodiment of a device 10 for limiting the flow rate at low differential pressures, particularly for limiting the inhaled volumetric flow during the inhalation of therapeutic aerosols. The device consists of an elongate square housing 11 formed with an upper plate-shaped housing half 12 and a lower plate-shaped housing half 13. The housing 11 consists of synthetic material.

An aspiration orifice 14, an inhalation orifice 15 as well as a ventilation bore 16 are formed in the upper plate-shaped housing element 12. A ventilation bore 17 is provided on the lower plate-shaped housing half 13 for precise alignment with the ventilation bore 16.

An upper silicone mat 13, a frame silicone mat and a lower silicone mat 20 are fastened between the plate-shaped upper and lower housing halves 12 and 13 in a manner not illustrated here, e. g. by screw connection on the edge side of the two plate-shaped housing elements 12 and 13.

Figure 4:
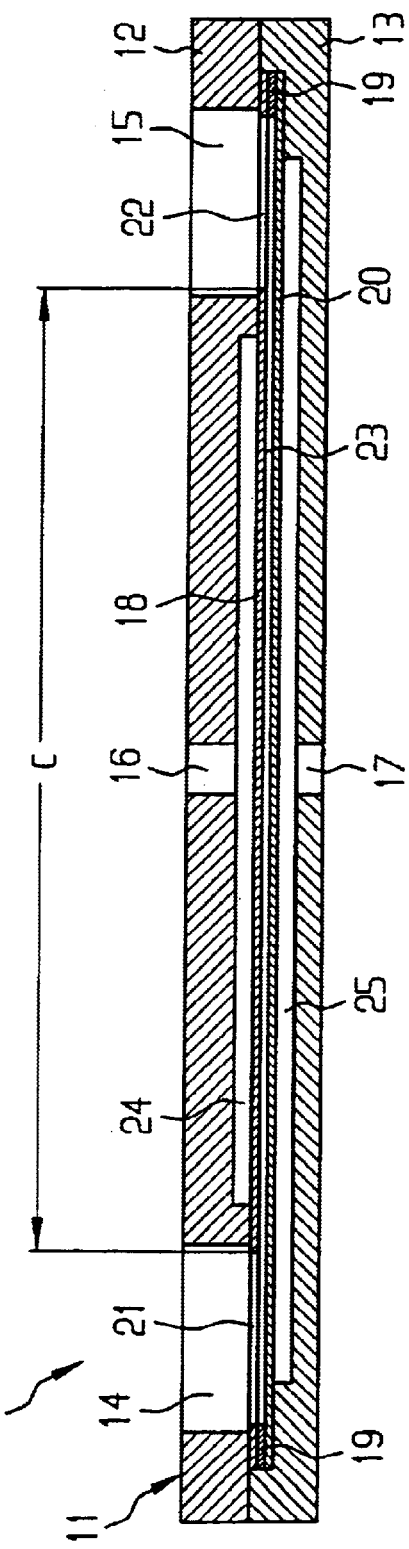
FIG. 4 is a sectional view along the line IV—IV in FIG. 1.
Figure 5:
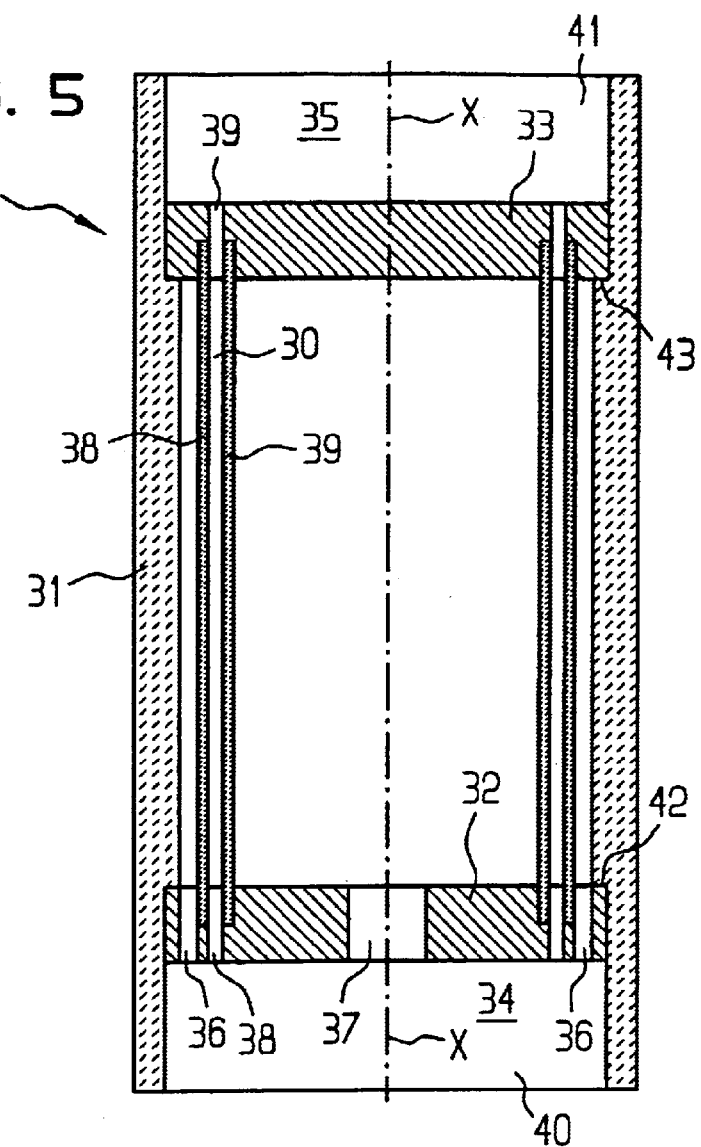
FIG. 5 illustrates a longitudinal section through another embodiment of a device for limiting the inhaled volume during the inhalation of therapeutic aerosols.
Figure 6:
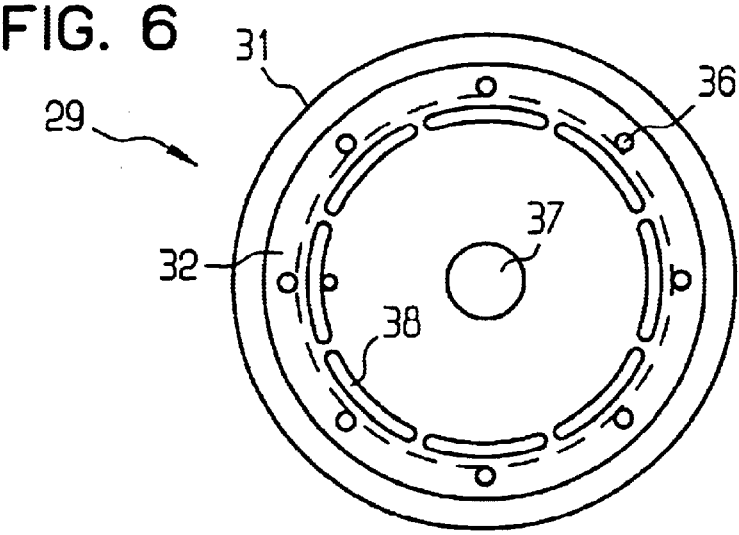
FIG. 6 is a view from below onto the device illustrated in FIG. 5.

As may be seen in FIG. 4, the upper silicone mat 13 has an opening 21 aligned with the orifice 14, as well as an opening 22 aligned with the inhalation orifice 15. As becomes evident in combination with FIGS. 3 and 4, a flow passage 23 is formed between the silicone mats 18 and 20 whilst a chamber-shaped recess 24 is provided oil the inner side of the upper plate-shaped housing half 12, which is open to the outside through the ventilation bore 16. A chamber-like recess 25 is formed on the outside of the lower silicone mat 20 in the lower plate-shaped housing half 13, which recess is exposed to the outside via the ventilation bore 17 and which extends laterally up to the zone of the openings 21 or 22, respectively. As is apparent from the sectional view in FIG. 3, the chamber 25 extends, however, in the respective longitudinal direction via the chamber 24 extending in parallel.

As is obvious from FIGS. 3 and 4, the flow passage 23 has a rectangular cross-section with a large width b, compared against a narrow height a corresponding to the thickness of the material of the silicone mat 19. The length c of the flow passage is indicated in FIG. 4.

When air is aspirated through the inhalation orifice 15 into the aspiration orifice 14 the flow resistance in the passage 23 creates a subatmospheric pressure. This negative pressure in the flow passage 23 ensures that the two silicone mats 18 and 20 will bend inwards, thus narrowing the cross-section of the flow passage. This bending of the silicone mats 18 and 20 is all the stronger the higher the negative pressure in the flow passage 23. The cross-section of the flow passage 23 hence varies as a function of the differential pressure between the inhalation orifice 15 and the aspiration orifice 14, and as the volumetric flow in its turn depends on the cross-section the volumetric flow is controlled directly via the change of the cross-section.

On account of the decreasing flexibility of the material the force, which the silicone mats 18 and 20 require for bending, rises, as the negative pressure in the flow passage increases, up to a limit which determines the desired minimum value of the flow passage cross-section for limiting the volumetric flow.

Due to the inventive concept the inventive device hence constitutes a flow rate control valve which controls the volumetric flow mechanically at pressure as low as 5 millibar. This flow control valve can hence be expediently used for limiting the inhaled volume in aerosol therapy. The device is superior to other known flow control systems in terms of both its function and the engineering expenditure, and is also suitable for universal application and individual adaptation to the respective requirements in terms of a limitation of the volumetric flow by an appropriate selection of materials and/or dimensioning of the a mats 18–20. The device is, of course, suitable not only for the field of aerosol therapy but can be used in all engineering fields wherever a flow rate limitation is desired at low differential pressures.

FIG. 5 shows another embodiment of a device 29 according to the present invention. The device vice 29 has a cylindrical housing 31 in which a flow passage 30 with an annular cross-section, which is spaced from the inside wall of the cylinder and arranged between radial retainer disks 32 and 33. The reference numeral 34 denotes the aspiration orifice on the housing 31 and the reference numeral 35 indicates the inhalation orifice on the housing 31. The flow passage 30 is formed with cylindrical silicone mats 38 and 39 which are inserted into the radial retainer disks 32 and 33.

The retainer disk 32 facing the aspiration orifice 34 comprises pressure equalizing bores 36 for the annular zone surrounding the flow passage, which bores are disposed at equal mutual spacings on a circle symmetrical relative to the longitudinal axis X—X of the cylindrical housing 31. A central pressure equalizing bore 37 is provided for the cylindrical interior zone inside the annular flow passage 30. The aerosol is aspirated in the region of the aspiration orifice 34 into the flow passage 30 through inlets 38 having the shape of ring segments whilst the retaining disk 33 has outlets 39 having the shape of ring segments. The retainer disks 32 and 33 are inserted into an inside section 40 or 41, respectively, of the cylindrical housing 31, which has an enlarged diameter, and bear against a shoulder 42 or 43, respectively, in a defined manner.

Figure 7:
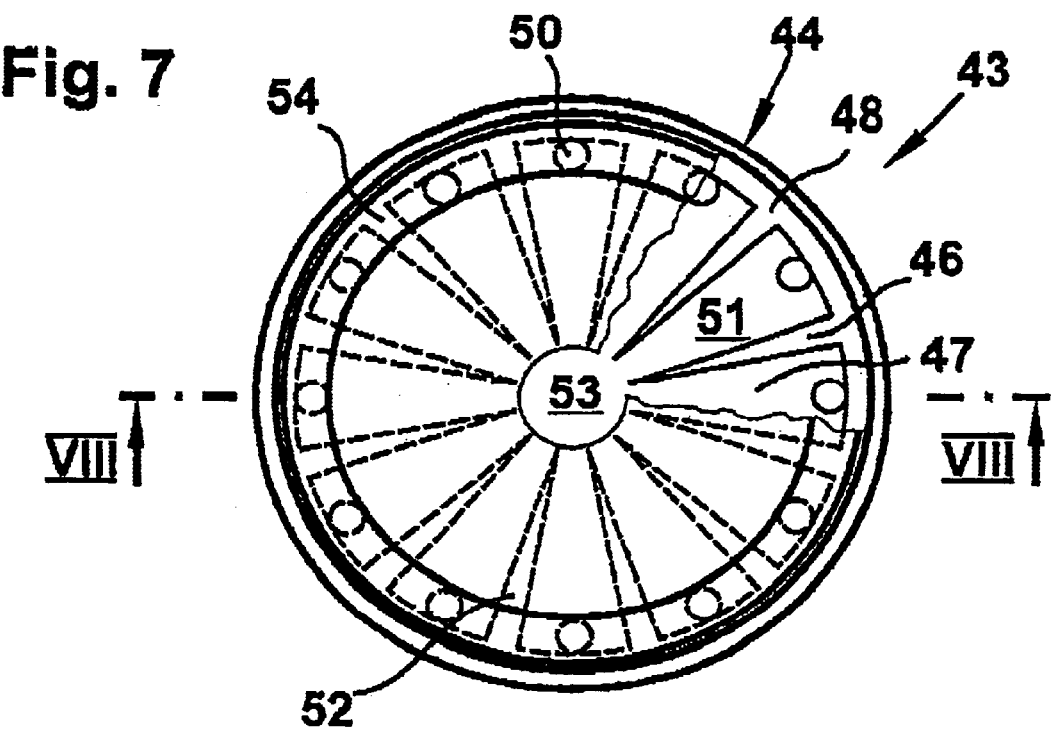
FIG. 7 is a plan view of another embodiment of an inventive device for flow rate limitation.
Figure 8:
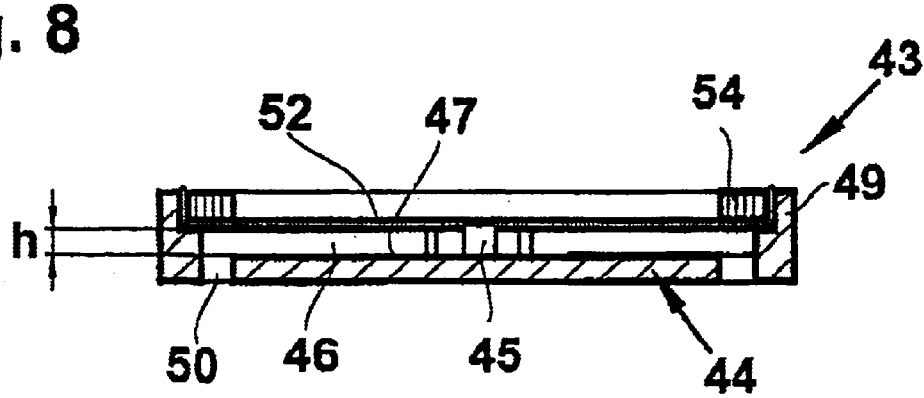
FIG. 8 is a section taken along the line VIII—VIII in FIG. 7.

FIG. 7 illustrates another embodiment of an inventive device 43 for flow rate limitation at low differential pressures, which is particularly well suitable for limiting the inhaled volumetric flow during inhalation of therapeutic aerosols. The device 48 consists of a disk-shaped basic body 44 in which, as may be seen in FIG. 8, a disk-shaped recess 45 with webs 46 integrally formed thereon is provided. The webs 46 are integrally formed on a flat bottom 47 of the recess 45 and extend over a height h up to a step 48 formed in the basic body 44. From this step 48, into which the webs 46 smoothly pass over, extends an integrally formed annular receiving part 49 extends upwardly over approximately the same height h. Near the outer edge, radially distributed aspiration orifices 50 are provided in the recessed part of the basic body 44, which are disposed between two adjacent webs 46 at the outer end of each flow passage 51. In the embodiment according to FIG. 7 the webs 46 are of equal lengths, radially disposed when seen from the middle of the housing and are flaring outwardly over their width.

Figure 9:
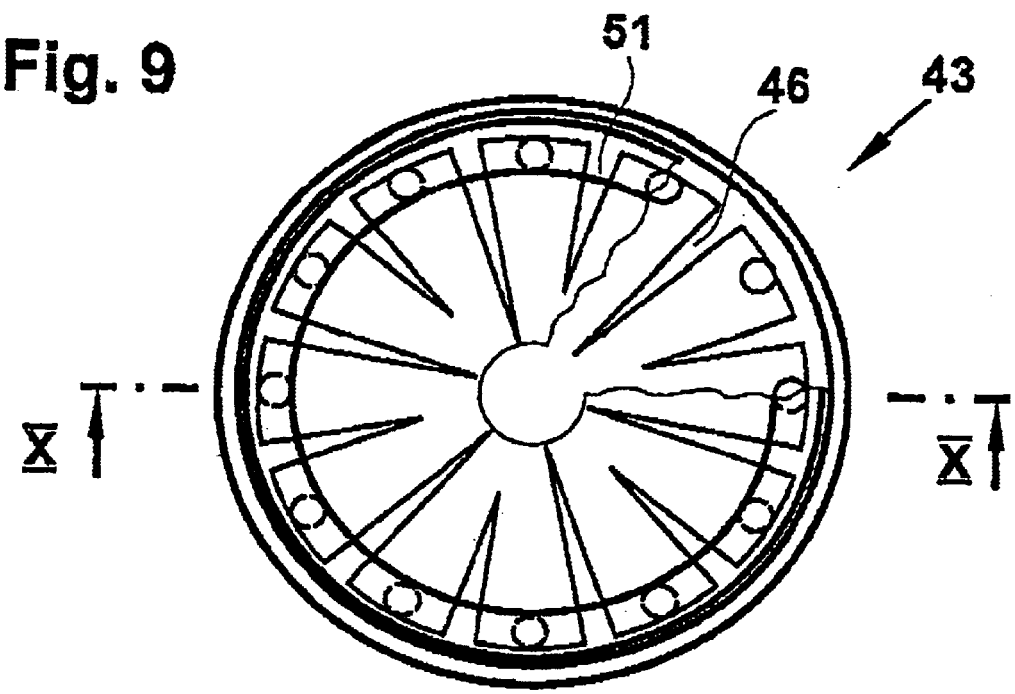
FIG. 9 is a plan view of a device modified in variation from FIG. 7, which present different web lengths.
Figure 10:
FIG. 10 is a section taken along the line X—X in FIG. 9.

In the embodiment according to FIG. 9 the differences reside in the fat that two different webs 46 and 51 are equidistantly arranged in alternation and are provided to taper towards the center, so that initially a wider flow passage is formed in the center of the housing 44, which is then split into two flow passage in a radially outward direction.

A thin flexible mat 52 is so disposed on the circular housing 44 that it rests on the webs and extends from 4 central opening 53 in the mat 52 outwardly over the step 48, with an upward deflection in the area of the receiving section 49. This thin flexible mat 52 consists, for instance, of silicone and is clamped on the edge side on the housing 44 by means of a fastening ring 54. The fastening ring 54 can be released from its positive-locking fastening position for replacement of the mat 52, and can then be used again.

Like the embodiment described by way of introduction for a linear flow rate limitation, wherein the flow passage can also be split into several flow passages, the embodiment of the device 43 for flow rate limitation according to the illustrations in FIGS. 7 to 10 operates also with only a single resilient wall or mat, respectively. The embodiment described last is provided with a so-called star-shaped structure having several flow passages 5 extending in a star-shaped configuration. The flow passages 51 originate from a center and are formed by the aforementioned flexible mat 52 on the upper side, on their sides by two webs 46 with a star-shaped extension, and on a lower planar surface 47. In this configuration, the webs 46 and the planar surface 47 are formed in one part. The aspiration orifice 53 is formed by an opening in the flexible mat 52, which extends up to the inner tips of the webs 46, whereas the inhalation orifices are formed by the lower part of the housing in The radial peripheral area.

The spacing of the elastic mat 52 from the planar surface 47 is defined by the height h of the webs 46. When air is aspirated through the aspiration orifice 53 the resulting flow resistance creates a pressure below atmospheric pressure in the flow regions formed b the flow passages 51. At the sane time, his pressure below atmospheric pressure draws the thin elastic mat 52 into the passage thus causing a restriction of the cross-section of the flow passage. Simultaneously, the deflection of the resilient mat 52 increases as the pressure in the flow passage 51 continues dropping below atmospheric pressure.

What is claimed is:

1. A device for flow rate limitation at low differential pressures, comprising a housing having at least one aspiration orifice, at least one inhalation orifice, and a flow region with at least one flexible wall disposed therebetween, which region has a cross-section which is adapted to be reduced, as a function of the differential pressure prevailing between said inhalation orifice and said aspiration orifice and of the flexibility of the material of each wall, down to a predefined size for predetermined volumetric maximum inhalation flow, wherein said housing further includes at least one ventilation opening defined therein at least in the central region between said aspiration and inhalation orifices, said at least one ventilation opening providing fluid communication between the environment and each wall.

2. The device according to claim 1, wherein said flow region comprises at least one flow passage having a flat elongate height by width cross-section.

3. The device according to claim 2, wherein the cross-section of each flow passage is formed to have opposing large-area walls.

4. The device according to claim 3, wherein the opposing large-area walls of each flow passage are fastened on an edge side in said housing.

5. The device according to claim 3, wherein said large-area walls present the same wall thickness.

6. The device according to claim 1, wherein each wall has a chamber section on its outside, at least in the central region between said aspiration and inhalation orifices, which section is open to the environment through a bore.

7. The device according to claim 1, wherein said flow region comprises at least one flow passage, and wherein each flow passage has a stratified structure.

8. The device according to claim 1, wherein said flow region comprises at least one flow passage, and wherein the flexible material used to form each flow passage consists of a biologically tolerable synthetic material.

9. The device according to claim 1, wherein said flow region comprises at least one flow passage, and wherein each flow passage has an integral structure.

10. The device according to claim 9, wherein each flow passage consists of a silicone component.

11. A device for flow rate limitation at low differential pressures, comprising a housing having at least one aspiration orifice, at least one inhalation orifice, and a flow region with at least one flexible wall disposed therebetween, which region has a cross-section which is adapted to be reduced, as a function of the differential pressure prevailing between said inhalation orifice and said aspiration orifice and of the flexibility of the material of each wall, down to a predefined size for predetermined volumetric maximum inhalation flow, wherein said flow region comprises at least one flow passage having a stratified structure, and wherein each flow passage is formed by a closed wall, a frame-shaped intermediate wall of the same size as the closed wall, and an equally sized wall including said aspiration and inhalation orifices.

12. A device for flow rate limitation at low differential pressures, comprising a housing having at least one aspiration orifice, at least one inhalation orifice, and a flow region with at least one flexible wall disposed therebetween, which region has a cross-section which is adapted to be reduced, as a function of the differential pressure prevailing between said inhalation orifice and said aspiration orifice and of the flexibility of the material of each wall, down to a predefined size for predetermined volumetric maximum inhalation flow, wherein said flow region comprises at least one flow passage, wherein the flexible material used to form each flow passage consists of a biologically tolerable synthetic material, wherein the cross-section of each flow passage is formed to have opposing large-area passage walls, and wherein at least said large-area passage walls consist of silicone mats.

13. The device according to claim 12, wherein each flow passage includes at least one material layer fastened for replacement between two housing sections.

14. A device for flow rate limitation at low differential pressures, comprising a housing having at least one aspiration orifice, at least one inhalation orifice, and a flow region with at least one flexible wall disposed therebetween, which region has a cross-section which is adapted to be reduced, as a function of the differential pressure prevailing between said inhalation orifice and said aspiration orifice and of the flexibility of the material of each wall, down to a predefined size for predetermined volumetric maximum inhalation flow, wherein each wall has a chamber section with a bore on its outside at least in the central region between said aspiration and inhalation orifices, with each of the respective bores of the walls communicating with said aspiration orifice through a passage.

15. A device for flow rate limitation at low differential pressures, comprising a housing having at least one aspiration orifice, at least one inhalation orifice, and a flow region with at least one flexible wall disposed therebetween, which region has a cross-section which is adapted to be reduced, as a function of the differential pressure prevailing between said inhalation orifice and said aspiration orifice and of the flexibility of the material of each wall, down to a predefined size for predetermined volumetric maximum inhalation flow, wherein said flow region comprises at least one flow passage having an annular cross-section, wherein each flow passage is symmetrically disposed in a cylindrical housing at a spacing from the inner walls of said cylinder, between radial retainer disks.

16. The device according to claim 15, wherein said retainer disks comprise inlets and outlets having the shape of ring segments, with the retainer disks including said inlets being provided with pressure-equalizing bores for a cylindrical interior space and an annular zone surrounding said flow passage.

17. A device for flow rate limitation at low differential pressures, comprising a housing having at least one aspiration orifice, at least one inhalation orifice, and a flow region with at least one flexible wall disposed therebetween, which region has a cross-section which is adapted to be reduced, as a function of the differential pressure prevailing between said inhalation orifice and said aspiration orifice and of the flexibility of the material of each wall, down to a predefined size for predetermined volumetric maximum inhalation flow, wherein said flow region comprises at least one flow passage having an annular cross-section, wherein each annular flow passage is formed by silicone mats.

18. A device for flow rate limitation at low differential pressures, comprising a housing having at least one aspiration orifice, at least one inhalation orifice, and a flow region with at least one flexible wall disposed therebetween, which region has a cross-section which is adapted to be reduced, as a function of the differential pressure prevailing between said inhalation orifice and said aspiration orifice and of the flexibility of the material of each wall, down to a predefined size for predetermined volumetric maximum inhalation flow, wherein said flow region is formed between a central aspiration orifice and inhalation orifices radially surrounding the central aspiration orifice as well as star-shaped webs extending from a common bottom surface to said at least one flexible wall and forming flow passages.

19. The device according to claim 18, wherein said webs present different lengths.

20. The device according to claim 18, wherein said webs are outwardly flaring over their width.

21. The device according to claim 18, wherein at least one inhalation orifice is provided between two adjacent webs.

22. The device according to claim 18, wherein a disk-shaped basic body is provided wherein said webs are integrally formed between flat recesses and inhalation orifices are formed on an edge side in said recesses, with a thin flexible mat with a central aspiration orifice resting on said webs and being fastened in an edge region of said basic body.

23. The device according to claim 22, wherein said mat is adhesively fastened, welded, or clamped by an annular assembly element in the edge region of said basic body.

24. The device according to claim 22, wherein said flexible mat comprises silicone, silicone rubber, Viton, latex, natural rubber or other elastomers.

25. A device for flow rate limitation at low differential pressures, comprising a housing having at least one aspiration orifice, at least one inhalation orifice, and a flow region with at least one flexible wall disposed therebetween, which region has a cross-section which is adapted to be reduced, as a function of the differential pressure prevailing between said inhalation orifice and said aspiration orifice and of the flexibility of the material of each wall, down to a predefined size for predetermined volumetric maximum inhalation flow, wherein each wall is open on its outside, at least in the central region between said aspiration and inhalation orifices, to the environment, and wherein said device is adapted such that substantially all flow between said aspiration orifice and said inhalation orifice is confined to a flow passage defined by the inside of each wall.

* * * * *

UNITED STATES PATENT AND TRADEMARK OFFICE
CERTIFICATE OF CORRECTION

PATENT NO.   : 6,681,762 B1
DATED        : January 27, 2004
INVENTOR(S)  : Scheuch et al.

It is certified that error appears in the above-identified patent and that said Letters Patent is hereby corrected as shown below:

Title page, Item [54] and Column 1, line 1,
Title, should read -- DEVICE FOR FLOW RATE LIMITATION AT LOW DIFFERENTIAL PRESSURES --

Title page,
Item [30], Foreign Application Priority Data, -- Mar. 19, 1999 (DE)   199 12 461.2 --

Signed and Sealed this

Twenty-ninth Day of June, 2004

JON W. DUDAS
*Acting Director of the United States Patent and Trademark Office*